(12) United States Patent
Hervy et al.

(10) Patent No.: US 6,746,398 B2
(45) Date of Patent: Jun. 8, 2004

(54) SYSTEM FOR THE REMOTE MONITORING OF PATIENTS

(75) Inventors: Robert Hervy, Jarville (FR); Laurent Romary, Essey-les-Nancy (FR); François Charpillet, Vandoeuvre-les-Nancy (FR); Jean-Marie Pierrel, Villers-les-Nancy (FR); Jean-Pierre Thomesse, Jarville (FR); Etienne PetitJean, Vandoeuvre (FR); Laurent Jeanpierre, Houdemont (FR); Pierre-Yves Durand, Nancy (FR); Jacques Chanliau, Neuves Maisons (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 16 days.

(21) Appl. No.: 10/262,291

(22) Filed: Sep. 30, 2002

(65) Prior Publication Data

US 2003/0069481 A1 Apr. 10, 2003

Related U.S. Application Data

(63) Continuation of application No. 09/539,988, filed on Mar. 30, 2000.

(30) Foreign Application Priority Data

Jan. 25, 2000 (FR) .............................. 00 00903

(51) Int. Cl.⁷ ................................. A61B 5/00
(52) U.S. Cl. ....................... 600/300; 128/920
(58) Field of Search .................. 600/300–301, 600/481–486, 500–508, 523, 529, 532, 538; 128/903–905, 920–925; 705/2–4; 706/924

(56) References Cited

U.S. PATENT DOCUMENTS 6,071,236 A    6/2000  Iliff
6,073,046 A    6/2000  Patel et al.
6,290,646 B1   9/2001  Cosentino et al.
6,454,705 B1   9/2002  Cosentino et al.

FOREIGN PATENT DOCUMENTS

FR          2 717 332         9/1995

OTHER PUBLICATIONS

Sven Koenig, R. G. Simmons, "Unsupervised Learning of Probabilistic Models for Robot Navigation", IEEE International Conference on Robotics and Automation 1996 Conference.

*Primary Examiner*—Charles Marmor
*Assistant Examiner*—Michael Astorino
(74) *Attorney, Agent, or Firm*—Blakely, Sokoloff, Taylor & Zafman

(57) ABSTRACT

System for monitoring patients at home comprising interface means at the patient's home, interface means at a doctor's surgery, a server linked by a network such as a telephone network to the interface means at the patient's home and to the interface means at the doctor's surgery, the said server receiving from the interface means at the patient's home, values of physiological parameters measured by the patient or by sensors and comprising means for storing a history, corresponding to a certain period of time, regarding the values of physiological parameters which are transmitted thereto, the said server furthermore comprising means for implementing a processing on the values of physiological parameters transmitted by the patient with a view to their presentation and to the presentation of their changes on the interface means at the doctor's surgery, characterized in that the said means implement on the latest values of physiological parameters which are transmitted to the server a processing comparing the state defined by these various values of physiological parameters with alert states defined as a function of the stored history of the patient and comprise means for transmitting the results of this processing to the interface means at the doctor's surgery.

19 Claims, 3 Drawing Sheets

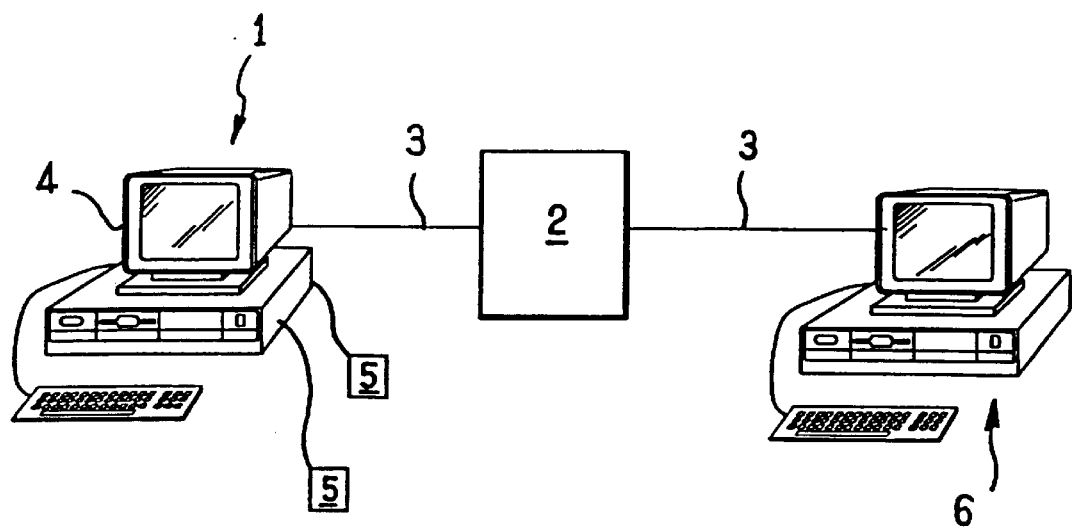
FIG_1
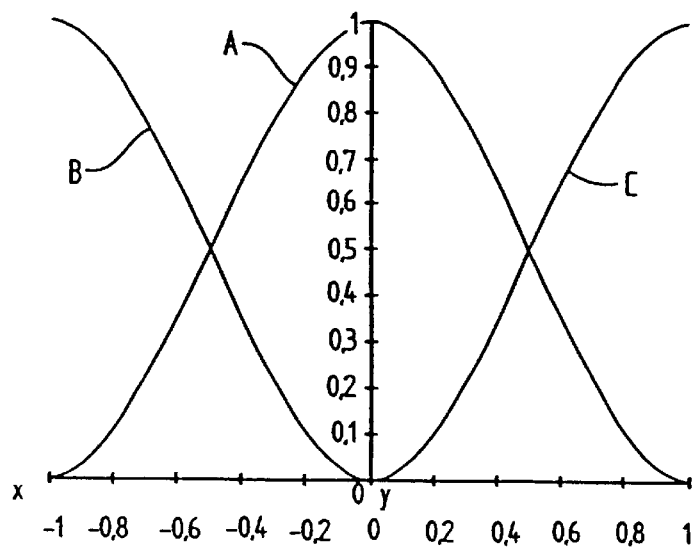
FIG_2

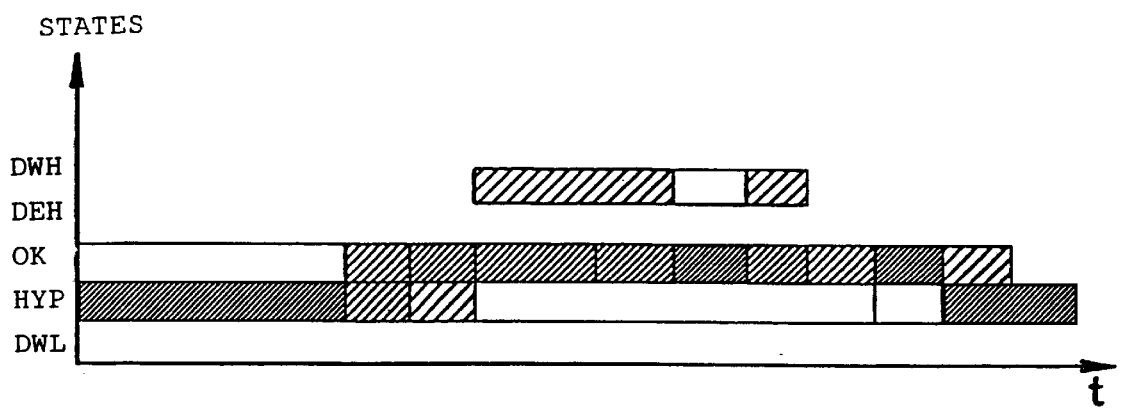
FIG_3
FIG_4

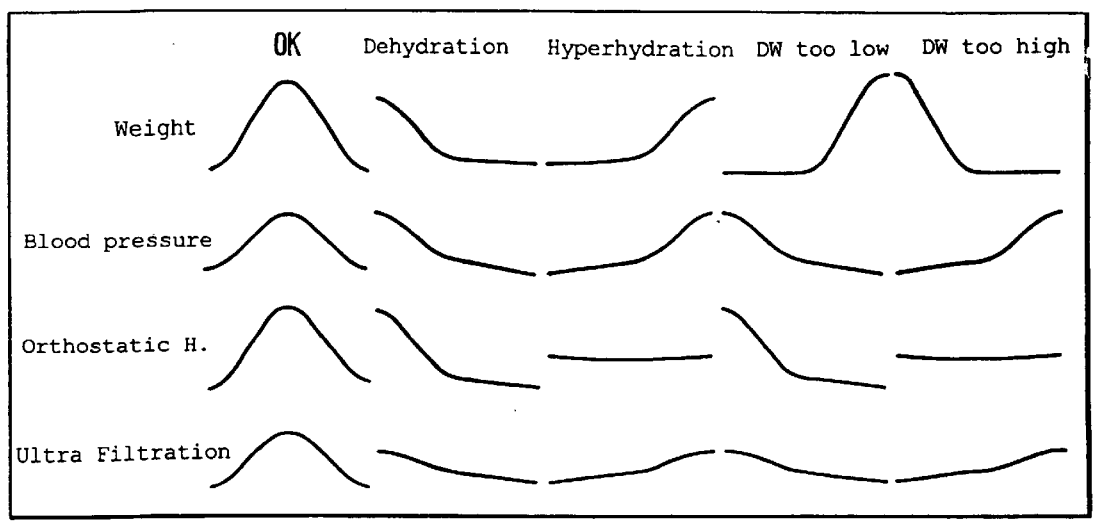
FIG_5

SYSTEM FOR THE REMOTE MONITORING OF PATIENTS

This is a continuation of application Ser. No. 09/539,988, filed Mar. 30, 2000.

BACKGROUND OF THE INVENTION

1. Field of the Invention

The present invention relates to a system for the remote monitoring of patients.

2. Description of the Related Art

Systems for remote medical monitoring are already known in which the patient is equipped with means via which he transmits to the doctor who is monitoring him values of physiological parameters allowing daily monitoring of the patient.

In this regard reference may for example be made to patent application FR 2 717 332.

SUMMARY

In the system described in this patent application, a processing is implemented on the data received from the patient, enabling the doctor to easily assimilate the data transmitted to him (presentations in the form of tables, graphics, statistics, etc.) and to reveal for him the changes in the physiological parameters measured over a certain period of time.

One object of the invention is to propose a system for the remote monitoring of patients which is further improved and constitutes for the doctor a genuine helpful tool which is able to reveal abnormal changes in the state of a patient and to do so with high reliability.

Another, more general, objective of the invention is to propose a system making it possible to improve the quality of the monitoring of patients, at the same time as their comfort, their safety, their relations with the medical world and which can also be used to help medical research.

Thus, the invention proposes a system for monitoring patients at home comprising interface means at the patient's home, interface means at a doctor's office, a server linked by a network such as a telephone network to the interface means at the patient's home and to the interface means at the doctor's office, the said server receiving from the interface means at the patient's home, values of physiological parameters measured by the patient or by sensors and comprising means for storing a history, corresponding to a certain period of time, regarding the values of physiological parameters which are transmitted thereto, the said server furthermore comprising means for implementing a processing on the values of physiological parameters transmitted by the patient with a view to their presentation and to the presentation of their changes on the interface means at the doctor's office, characterized in that the said means implemented on the latest values of physiological parameters which are transmitted to the server a processing comparing the state defined by these various values of physiological parameters with alert states defined as a function of the stored history of the patient and comprising means for transmitting the results of this processing to the interface means at the doctor's surge.

Such a system is advantageously supplemented by the following various characteristics taken alone or according to all their possible combinations:

- the said processing means compare the values of physiological parameters or values of other parameters determined as a function of the latter values with threshold values which are determined as a function of the stored history and, when such a threshold value is exceeded, transmit an alert message to the interface means at the doctor's surgery and/or at the patient's home;
- the processing means determine values of parameters referred to as trend parameters which are dependent on the latest values of physiological parameters transmitted via the interface at the patient's home and on a part of the stored history which just precedes in time the transmission of these latest values of physiological parameters, compare these values of trend parameters with threshold values and, when such a threshold value is exceeded, transmit an alert message to the interface means at the doctor's office and/or at the patient's home;
- at least a part of the latest values of physiological parameters transmitted by the interface at the patient's home are furthermore compared with other threshold values which is independent of the history and in that the value of at least one trend parameter is modified when one of these threshold values is exceeded;
- the processing means determine with regard to the latest values of physiological parameters which are transmitted to the server, and as a function of the history of the patient, the probabilities of occupying a given alert state, the probabilities thus determined for the various possible states for the patient being transmitted to the interface means at the doctor's surgery;
- the server comprises means for, when a patient seeks to connect up, identifying the said patient, interrupting the communication and connecting up to the interface means of the said patient;
- the interface means at the patient's home enable the latter to transmit information to the doctor only when the patient has filled in a chart of daily parameters;
- the interface means at the patient's home comprise means for checking the consistency of the physiological parameter values measured and transmitted by the patient.

BRIEF DESCRIPTION OF THE FIGURES

Other characteristics and advantages of the invention will emerge further from the description which follows. This description is purely illustrative and non-limiting. It should be read in conjunction with the appended drawings in which:

FIG. 1 is a diagrammatic representation illustrating an operational architecture of a system in accordance with one possible embodiment of the invention;

FIG. 2 is a graph on which are plotted curves which illustrate functions used by the server of the system of FIG. 1;

FIG. 3 and FIG. 4 are two graphs illustrating two possible modes of presenting the results of the processing of the server at the level of the interface means at the doctor's office;

FIG. 5 is a graph on which are plotted various curves used in the calculation of the probabilities.

DETAILED DESCRIPTION OF THE INVENTION

General Architecture

The system which is illustrated in FIG. 1 comprises interface means 1 arranged at the patient's home, a computer server 2 with which the means 1 talks by way of the telephone network, referenced by 3, and interface means 6 arranged at the doctor's office.

The means 1 at the patient's home consist of a computer terminal 4 which may possibly be linked to sensors 5 which make it possible automatically to record values of physiological parameters of the patient.

The patient exchanges for example daily with the server 2 using the means 1.

For this purpose, when the patient has connected up to the server 2 via his telephone line, he identifies himself by providing the server 2 with an identification code, together with a password.

The communication is then interrupted and the patient is called back by the server 2.

As will have been understood, this breaking down of the connection into two steps, and in particular the fact that the server calls the patient back after the latter has identified himself, enables the use of the system to be made secure.

Once the connection has been re-established, a first screen presents the patient with the messages which his doctor was able to leave for him.

Once the patient has assimilated these messages, he is asked to fill in a chart of daily parameters wherein he must indicate, for the physiological parameters whose values are not transmitted automatically by the sensors, the values of the physiological parameters which he has been able to measure himself.

The computer terminal 4 then implements a processing making it possible to check the consistency of the value entered for each parameter.

For example, he compares the value of the parameters with threshold values.

When all the headings of the chart have been filled in—and only in this case—, the set of measured physiological parameter values is transmitted to the server 2.

The means 6 consist for their part of a straightforward computer terminal which receives the results of a processing implemented by the server 2.

This processing is intended to present to the doctor the latest measured values of physiological parameters and as appropriate to detect and reveal to the doctor any abnormal change in these parameter values.

It will be noted that when an abnormal change of this type is detected, the latter is immediately signaled to the patient so that he can, on his own account, contact the doctors who are monitoring him.

Possible examples of processing will now be described in the case where the system is used for monitoring home dialysis and in particular for monitoring patients subjected to continuous ambulatory peritoneal dialysis (CAPD).

Of course, other applications of the system proposed by the invention may be envisaged, the application to the monitoring of patients subjected to continuous ambulatory peritoneal dialysis being regarded as merely one example from among other possible examples.

The processing implemented by the server 2 is an expert-system processing which is customized as a function of the history of the patient.

In particular, the server 2 stores in memory the values of the physiological parameters of the patient and data calculated from the latter over a duration which may be sixteen days.

First Example of Processing

A processing in accordance with a first possible example is a processing which on the one hand implements a determination of alerts with regard to parameters referred to as trends which are dependent on the history of the patient and on the other hand implements a detection of alerts on the basis of various processing rules regarding the values of physiological parameters just transmitted by the patient.

The trend parameters are for example the hydration, the temperature, supine blood pressure and the upright blood pressure, the values of drainage volume for the bags.

Each day the hydration trend is attenuated by a factor 1.5 and increased by a value equal to 25 times the ratio between the ideal body weight deviation divided by 1.5. This value is significant when the ideal body weight deviation is greater than 1.5 KG (1.5 being the tolerance on the weight).

The values of these trend parameters are determined as a function of the recent history, as for example averaged over a duration of a few days, and are compared with an alert triggering threshold, which is dependent on the normal values of the patient.

It is understood that on account of the fact that the trend parameters are calculated by taking into account not only the latest values received from the patient, but also the values over the duration corresponding to that chosen for the recent history, the trend parameters will generate alerts only in the cases where the physiological parameters have deviated from their normal value not only pointwise at a given instant, but over a certain duration (that of the recent history).

Thus, for example, if a patient has a temperature of 38°, this has no pointwise consequence, but becomes worrying if this temperature is maintained for a certain time.

The processing proposed makes it possible to trigger an alert signal making it possible to reveal this "long-term" drift.

For example, one trend used is a hydration trend.

The hydration trend is a number between −99 and +99 which reflects the degree of hyperhydration when it is positive and the degree of dehydration when it is negative.

When the hydration is normal, the trend is close to zero.

The hydration trend is initialized to 0. When its absolute value exceeds 100 a "Major" alert is generated. The latter will be indicated to the patient, and will appear as a priority on the doctor interface. This occurs only when several symptoms corroborate one and the same diagnosis, or when one and the same factor is repeated several days running.

The hydration trend is incremented by +30 when the weight-hydration-relation rule is triggered, by −30 when the weight-dehydration-relation rule is triggered, −25 when the lying-standing-difference rule is triggered.

Each day the hydration trend is attenuated by a factor 1.5 and increased by a value equal to 25 times the ratio between the dry weight deviation divided by 1.5. This value is significant when the dry weight deviation is greater than 1.5 KG (1.5 being the tolerance on the weight).

It will be noted that the normal values which are used are themselves dependent on the history of the patient over a greater duration. They are for example determined by calculating the mean value of the relevant parameter over a duration of sixteen days.

Moreover, the values of trend parameters are furthermore modified, as is described hereinbelow, as a function of the state of the patient such as results from the physiological parameter values transmitted last by the patient, and in particular upon detecting alert states with regard to these parameters.

The processing for detecting alert states with regard to the physiological parameter values transmitted last for its part implements the following rules:

WEIGHT-DEHYDRATION-RELATION: this first rule checks whether the weight of the patient exceeds his ideal body weight. The limit fixed by the doctors is 1.5 Kg If this limit is overstepped, a "Hyperhydration" alert is triggered, and a penalty of 30% is added to the HYDRATION trend.

WEIGHT-DEHYDRATION-RELATION: this rule is the symmetrical counterpart of the previous rule. This one checks whether the weight goes below the ideal body weight. (a tolerance of 1.5 Kg is likewise accepted.) In this case, a "Dehydration" alert is triggered, and a penalty of 30% is deducted from the HYDRATION trend.

LYING-STANDING-DIFFERENCE: this rule monitors the difference between the blood pressure of the patient when standing, and the blood pressure of the patient when lying. At normal times, this difference is relatively small. When the patient begins to dehydrate, this value goes wild. An arbitrary limit of 1.5 has been fixed. The test is performed on the difference between the average blood pressures of the two positions (standing and lying). If the limit is exceeded, a "Dehydration" alert is triggered, and a penalty of 25% is docked from the HYDRATION trend.

PRESSURE-LYING-VARIATION: this rule monitors the variations in the blood pressure of the patient when lying. This test is performed on the mean of the systolic and diastolic pressures, from which is subtracted the mean value over time of this value for the patient. When an arbitrary limit of 1.5 is exceeded, a "Fast modification lying pressure" alert is generated. However, and unlike with the other rules of this group, no penalty is inflicted on the trends. This is because it seems to have no direct relationship with the state of the patient, except perhaps that this kind of alert indicates that all is not well with him!

PRESSURE-STANDING-VARIATION: this rule is the symmetrical counterpart of the previous rule. This one checks the variations in the blood pressure of the patient when standing. For the remainder, its behavior is strictly identical.

BAG_1, BAG_2, BAG_3, and BAG_4: these four rules check the volume drained by each of the patient's four bags. According to the type of bag, the volume drained should remain almost constant, even if large variations are possible. This is why no alert is attached to these rules. The latter are therefore responsible simply for updating the BAGS trend as a function of the volumes observed. This editing is carried out on the basis of the following formula which has been determined empirically:

(((bag out-bag in)—mean value of this type of bag)/200)*15)= New value of bag parameter After determining these various alert states, the system updates the normal values used for managing the trend parameters, that is to say determines the new normal values to be taken into account during the next processing, and does so by calculating new mean values over the entire history, these new mean values integrating the latest values of physiological parameters transmitted by the patient.

Second Example of Processing

A second possible processing by expert system will now be described.

This processing has been developed on the basis of a partially observable Markovian decision process (POMDP) model.

Theoretical Overview.

Conventionally, a model is expressed in the form of an n-tuple <S, A, O, B, T, R, Π> in which:

S represents the finite set of states of the environment which one seeks to model. When these states are not directly observable, a model of the observations must be defined. This model comprises a finite set O of possible observations and an observation function B which has a state of S or more generally with a pair (state, action) associates a probability distribution over the elements of O. B(o | s, a) represents the probability of observing o∈O from the state s (having taken the action a).

A is the finite set of actions which make it possible to influence the process. These actions are intended to make the system change from one state to another. The actions have an uncertain effect which is modeled by the transition function defined below.

O is the finite set of observations which makes it possible to characterize the model.

B is the observation function

T is the transition function which defines the probability of going from state s to state s' by performing the action of A.: p(s' | s, a)

R is the reward function which associates with each state, or with each pair (state, action) a number which expresses the degree of satisfaction of placing the system in state s, or of choosing the action a when one is in state s.

Π gives the initial probability distribution over the set of states.

A model expressed in this form can be exploited by an automatic system so as to answer the following questions:

given a sequence of observation vectors ($o_1 \ldots o_T$) what is the probability that the system occupies the state s at the instant T (diagnosis).

given a sequence of observation vectors ($o_1 \ldots o_T$) and a model λ, how does one adjust the parameters <B, T, Π> so as to maximize $p(o_1 \ldots o_T|\lambda)$ (learning).

given a sequence of observation vectors what is the optimal action to be undertaken so that the system reaches a given state (recommended action).

Such a model is for example of the type of those described in the publication:—Koenig, R. G. Simmons in "Unsupervised Learning of Probabilistic Models for Robot Navigation" published in the proceedings of the IEEE ICRA'96 conference.

Application of Such a Model to the Processing Proposed for Monitoring Hydration.

Definition of the Elements of the Model

The states of the set S which are used are five in number: normal hydration, dehydration, hyper-hydration, underestimated ideal body weight and overestimated ideal body weight.

The observations of the set O for their part consist, for each physiological parameter, of the following indicative symbols O(i): satisfactory$_i$, below-the-norm$_i$, above-the-norm$_i$, where i is an index which according to its value denotes one or other of the physiological parameters.

The physiological parameters considered are weight, blood pressure, orthostatic blood pressure and balance sheet for the bags, which parameters can be readily calculated from the chart which is teletransmitted daily.

More precisely, to determine whether the weight is satisfactory, below the norm, above the norm, the variation in the difference between the weight of the patient and the ideal body weight fixed by the doctor is monitored.

In particular, this difference is compared with lower or upper threshold values which are for example plus or minus 1.5 kg.

To determine whether the blood pressure is satisfactory, below the norm or above the norm, the variations in the difference between the latest blood pressure transmitted and a mean blood pressure calculated over the stored history of the patient are monitored.

In particular, this difference is compared with threshold values which are for example plus or minus 1.2.

Likewise, to determine whether the orthostatic blood pressure is satisfactory, below the norm, above the norm, the difference between the blood pressures of the patient when he is lying and when he is standing is determined. The normal has been fixed at 0.5, the tolerance at 1.5.

Lastly, to determine whether the balance sheet for the bags is satisfactory, below the norm or above the norm, the difference between the volume drained by the bags of the patient and a mean drained volume determined over the history of the patient is determined.

The normal value is zero, that is to say that on average, bags of one type almost always give the same flows. The tolerance has been fixed at 60%. This tolerance is relatively high, since too many parameters are beyond our control for this to be truly reliable.

It will be noted that in the case of monitorings which involve averaging over the history of the patient, this history is for example fifteen days.

The observation function B for its part represents the probability of observing, for a given physiological parameter i, one of the qualitative symbols of the set O, knowing the state s of the system.

It is understood, if one refers to the definition of the qualitative observation symbols, that these symbols are not directly accessible on the basis of the data transmitted to the server.

The system therefore implements a processing making it possible to estimate the probability of observing a value $V_{i,t}$ in respect of a given physiological parameter i and in respect of a given time t, assuming that the state occupied by the system is known.

This probability is expressed as follows:

$$v_{i,t}:p(v_{i,t}|s)=\Sigma_{o \in o(i)} f_{s,o}(v_{i,t}) p_i(o|s)$$

where f is a function of the type of that illustrated in FIG. 2 which gives a weighting of between 0 and 1 and which is dependent on the value of the physiological parameter i for a given state s.

For example, for the satisfactory state complying with the norm, the change in this function versus the value of the physiological parameter will be of the type of that illustrated in curve A in FIG. 2.

For the below the norm indicative observation, the function will have the form represented by the curve B in FIG. 2.

For the above the norm indicative observation, the function will have the form of the curve C in FIG. 2.

These various curves A, B, C are in this instance sigmoides.

The curves A, B and C are curves defined as a function of the ratio (measured value—base value)/tolerance, where the base values and the tolerance values are, as was defined previously, values defined by the doctor or dependent on history.

The probabilities defining the transition functions T for their part have been determined empirically.

It is brought in when calculating the probability distribution over the five states modeled by the model defined for the monitoring of hydration.

Let b be this probability distribution over S. b(s,t) is the probability that the patient is in the state s at the instant t. The probability that the patient is in the state s' at the instant t+1 can be estimated by knowing the observation o(t+1) and the action a(t) through the formula:

$$p(s'|b,a,o) = \frac{p(o|s',a,b)p(s'|a,b)}{p(o|a,b)} = \frac{p(o|a,s')\sum_{s \in S} p(s'|a,s)b(s)}{p(o|a,b)}$$

with $p(o|a,b) = \sum_{s' \in S} p(o|a,s') \sum_{s \in S} p(s'|s,a)b(s)$ and $p(o|a,s) = \prod_{i \in I} p(v_i|s)$ The actions A and the reward function R are optional.

Processing Implemented on the Elements thus Defined

With the model just described, the processing implemented by the server 2 which receives the information from the patient is as follows.

Once the values $V_{i,t}$ of the various physiological parameters i have been acquired in respect of the time t, the observation vector consisting of these various values is processed so as to determine the probabilities of occupying the state s, doing so for each of the states. For example, the probability of occupying a given value $v_{i,t}$ for the orthostatic tension is calculated from the following equation:

$$p(v_{i,t}|normal) = 5\% * s -$$

$$\frac{-v_{i,t} - 0.5}{1.2} \sqrt{\leftarrow} + 83\% * bell \frac{-v_{i,t} - 0.5}{1.2} \sqrt{\leftarrow} + 12\% * s + \frac{-v_{i,t} - 0.5}{1.2} \sqrt{\leftarrow}$$

for i–orthostatic,

S–the sigmoid defining "below-the-norm$_i$" (FIG. B),

S+the sigmoid defining "above-the-norm$_i$" (FIG. C), bell the Gaussian defining "satisfies the norm$_i$" (FIG. A)

The Values of 5%, 83% and 12% correspond to the probabilities that is orthostatic tension is observed to be below the norm, to satisfy the norm or to be above the norm, these probabilities being determined as a function of the history of the patient.

The values of 0.5 and 1.2 correspond to those of the normal reference and of the tolerance for this parameter.

FIG. 5 presents the various curves obtained in this way for the four physiological parameters considered and the five states of the model.

Once these probabilities have been determined, the probability of occupying a given state is deduced from them, taking into account the set of values measured for the physiological parameters.

The information item thus determined is thereafter converted so as to be presented to the doctor.

For example, as illustrated in FIG. 3, this presentation can be done as a function of various gray levels for the various states considered.

It can also be presented in numerical form, as illustrated in FIG. 4. On the graph of this FIG. 4 is represented a plurality of curves which each represents the change as a function of time of the probabilities of occupying the normal state for one of the parameters i.

In each case, the information item is presented in a temporal manner.

It will be noted that the doctor has the possibility of modifying the profiles of gray levels or of probability values which are presented to him for the various states, if he estimates that the diagnosis does not correspond to his own.

Let us assume for example that the trend which appears in the middle of the graphic (the Dry-Weight is certainly too low) is a false alert, and that the sufferer remains hyperhydrated the whole time. The doctor will simply 'grasp' the curve by the 'handles' (the framed points) and move them with a view to putting them back where they ought to be. The result of this process is a new profile, but the latter no longer has any relationship with the data input by the patient.

Hence, the algorithm will thereafter try to learn the relationship between the instruction which it has just received, and the data available to it so as to propose a viable solution. The latter should be as close as possible to the instruction provided by the doctor, but it should be generated by the underlying Markovian model. In this way, a relationship between the data provided by the patient and the profile is recovered. This naturally leads to compromises.

It will be noted that the adaptation processing consists of modifications of the values determined for the probabilities $p_i(o/s)$, which modifications are calculated in such a way as to minimize the error between the new solution proposed by the doctor and the solution provided by the model.

It will be noted that this processing amounts to determining 40 parameters for the set of states under the constraint of minimizing the aforesaid error.

Indeed, the functions $f_{s,o}$ being given, only the parameters $t_i(o/s)$ need to be determined. Consequently this amounts to determining $12=3\times 4$ probability values for each state, under the constraints $p_i(\text{below-the-norm}_i|s)+\text{pi}(\text{satisfactory}_i|s)+\text{pi}(\text{above-the-norm}_i|s)=1$, i.e. in total 8 unknowns to be determined per state.

What is claimed is:

1. A system for monitoring patients subjected to dialysis at home comprising:
   interface means at the patient's home:
   interface means at the doctor'surgery;
   a server linked by a network to the interface means at the patient's home and to the interface means at the doctor'surgery for receiving from the interface means at the patient's home a value of physiological parameter measured by the patient or by sensors;
   means for storing a history on the server, the history comprising values of the physiological parameter taken over a period of time;
   means for implementing a processing on the server on the value of the physiological parameter for presentation and for presentation of their changes to the interface means at the doctor's surgery, wherein the means for implementing a processing implements on the latest value of the physiological parameter which is transmitted to the server a processing comparing the latest value of the physiological parameter which is transmitted to the server a processing comparing the latest value with an alert state for generating a result;
   means for transmitting the result to the interface means at the doctor's surgery; and
   wherein the means for implementing a processing calculate the probability for the patient to be in a given state among five possible states: normal hydration, dehydration, hyper-hydration, underestimated dry weight and overestimated dry weight.

2. A system according to claim 1, wherein the means for implementing a processing compares the value of the physiological parameter or a modified physiological parameter with threshold values determined as a function of the history and, when such a threshold value is exceeded, transmits an alert message to the interface means at the doctor's office and/or at the patient's home.

3. A system according to claim 1, wherein the means for implementing a processing determines a trend parameter value, compares the trend parameter value with a threshold value and, when the threshold value is exceeded, indicates an alert message to the interface means at the doctor's office and/or to the interface means at the patient's home.

4. A system according to claim 3, wherein the means for implementing a processing compares more than one latest value with other threshold values which are independent of the history for modifying at least one trend parameter when one of the other threshold values is exceeded.

5. A system according to claim 4, wherein the means for implementing a processing determines the probability of occupying a given state as a function of a ratio between on the one hand a difference between the value of the physiological parameter and a normal reference value for the physiological parameter considering a tolerance.

6. A system according to claim 5, wherein the reference value is dependent on the history.

7. A system according to one of claim 1, wherein the interface means at the doctor's office enables modification of the calculation of the probability of occupying a given state by the means for implementing a processing by means of modified calculation values proposed by the doctor.

8. A system according to claim 1, wherein the server comprises means to identifying the patient, interrupting the communication and then connecting up to the interface means at the patient's home.

9. A system according to claim 1 wherein the interface means at the patient's home requires the patient to fill in a chart of daily parameters prior to sending the physiological parameters.

10. A system according to claim 1 wherein the interface means at the patient's home comprise means for checking the consistency of the physiological parameter values measured and transmitted by the patient.

11. A system according to claim 1, wherein the server links to the interface means at the patient's home and the interface means at the doctor's office via a telephone network.

12. A method for monitoring a patient subjected to dialysis at home comprising:
   comparing a difference between a latest weight of the patient and an ideal body weight for the patient with a weight threshold and updating a weight trend in a server;
   comparing a difference between a supine blood pressure of the patient and an upright blood pressure of the patient with a lying-standing blood pressure difference threshold and updating a lying-standing blood pressure trend in the server;
   comparing a mean of the supine systolic pressure and a supine diastolic pressure with a supine pressure-lying-variation threshold calculated as the mean value over time of the mean of the supine systolic pressure and the supine diastolic pressure for the patient and updating a lying blood pressure trend in the server;
   comparing the mean of the upright systolic and an upright diastolic pressure with a pressure-standing-variation threshold calculated as the mean value over time of the mean of the upright systolic pressure and the mean of the upright diastolic pressure for the patient and updating an upright blood pressure trend in the server;
   determining a values of bags parameter based on volumes observed in a plurality of bags and updating a values of drainage volume of bags trend in the server;
   transmitting an alert message from said server to an interface means at a doctor's office and/or to an interface means at a patient's home if a threshold value is exceeded; and wherein threshold values are determined as a function of a stored history and are updated trend data received by the server.

13. A method according to claim 12, further comprising:

initializing a hydration trend to zero;

incrementing the hydration trend by a first given value when the weight of the patient exceeds his ideal body weight over a high weight threshold;

incrementing the hydration trend by a second given value when the weight of the patient goes below his ideal body weight under a low weight threshold;

incrementing the hydration trend by a third value when the difference between an upright blood pressure of the patient and a supine blood pressure of the patient exceeds a given lying-standing blood pressure difference threshold; and attenuating the hydration trend daily by a factor and increasing the hydration trend daily by a value proportional to an ideal body weight deviation.

14. A method according to claim 12, whereby the value of a bag trend is determine as follows:

$$Bag = \left((Bag_o - Bag_i) - \frac{\langle Bag \rangle}{200}\right) \times 15$$

where Bag is the new value of bag parameter, $Bag_i$ is the volume that enters the bag, $Bag_o$ is the volume that goes out the bag, <Bag> is the mean value of the volume contained in this type of bag.

15. A method for monitoring a patient subjected to dialysis at home comprising:

calculating a probability of observing a given value $v_{i,t}$ for a physiological parameter in a server from the following equation:

$$P(V_{i,t} | S) = \sum_{o \in O(i)} f_{s,o}(V_{i,t}) p_i(o | s)$$

where $V_{i,t}$ is a value observed for a physiological parameter at the time t, O(i) is a set of possible observations for the physiological parameter i, said set (O(i) comprising observations, including satisfactory, below a norm value, above a norm value;

f is a function of the type which gives a weighting of between 0 and 1, which is dependant on the value of the physiological parameter i for a given state s, and which parameters are defined by a doctor or depend on history, $p_i(o|s)$ is the probability of observing o for the parameter i assuming that the state of the patient is s; and transmitting an alert message from said server to an interface means at a doctor's surgery and/or to an interface means at a patient's home if the norm value is likely to be exceeded;

wherein norm values are determined as a function of a stored history and are updated trend data received by the server.

16. A method according to claim 15, whereby the physiological parameter is selected from the group consisting of weight, blood pressure, orthostatic blood pressure, or balance sheet for the bags.

17. A method according to claim 16, further comprising:

comparing the difference between the weight of the patient and an ideal body weight with a lower and an upper weight threshold values;

comparing the difference between the blood pressure and a mean blood pressure calculated over a history of the patient with a blood pressure threshold value;

comparing the difference between the upright and supine blood pressures of the patient with a threshold value;

comparing the difference between a volume drained by the bags of the patient and a mean drained volume determined over a history of the patient with a normal value; and deducing for each parameter i selected from the group consisting of weight, blood pressure, orthostatic blood pressure, or a balance sheet for the bags, a corresponding observation o in O(i).

18. A method according to claim 15, whereby the function f depends on a ratio defined by: (measured value for i–base value for i)/ tolerance, where the base value and the tolerance value for the parameter i are defined by a doctor or depend on a history.

19. A method according to claim 15, comprising modifying the values determined for the probabilities $p^i(o|s)$, which modifications are calculated in such a way as to minimize the error between a new solution proposed by the doctor and the probability of observing a value for the physiological parameter calculated in the server.

* * * * *

UNITED STATES PATENT AND TRADEMARK OFFICE
CERTIFICATE OF CORRECTION

PATENT NO. : 6,746,398 B2
DATED : June 8, 2004
INVENTOR(S) : Hervy et al.

It is certified that error appears in the above-identified patent and that said Letters Patent is hereby corrected as shown below:

Column 9,
Lines 32 and 35, please delete "doctor'surgery;" and insert -- doctor's surgery --.

Signed and Sealed this

Twenty-eighth Day of December, 2004

JON W. DUDAS
*Director of the United States Patent and Trademark Office*